United States Patent [19]
Agouridas et al.

[11] Patent Number: 5,635,485
[45] Date of Patent: Jun. 3, 1997

[54] ERYTHROMYCIN COMPOUNDS

[75] Inventors: Constantin Agouridas; Jean-Francois Chantot, both of Nogent sur Maine; Alexis Denis, Paris; Solange G. D'Ambrieres, Paris; Odile L. Martret, Paris, all of France

[73] Assignee: Roussel Uclaf, France

[21] Appl. No.: 426,067

[22] Filed: Apr. 21, 1995

[30] Foreign Application Priority Data

May 3, 1994 [FR] France ................... 94 05368

[51] Int. Cl.$^6$ .................. A61K 31/70; C07H 17/08
[52] U.S. Cl. ................ 514/29; 536/7.2; 536/7.3; 536/7.4
[58] Field of Search ............... 536/7.2, 7.3, 7.4; 514/29

[56] References Cited

U.S. PATENT DOCUMENTS

| | | | |
|---|---|---|---|
| 5,403,923 | 4/1995 | Kaulimura et al. | 536/7.2 |
| 5,527,780 | 6/1996 | Agouridas et al. | 536/7.4 |

FOREIGN PATENT DOCUMENTS

| | | |
|---|---|---|
| 0487411 | 5/1992 | European Pat. Off. . |
| 0596802 | 5/1994 | European Pat. Off. . |
| 0606062 | 7/1994 | European Pat. Off. . |
| 0606024 | 7/1994 | European Pat. Off. . |
| 2692579 | 12/1993 | France . |

OTHER PUBLICATIONS

Copy of J. Org. Cgem. 1988 53, 2340–2345 No. 10, Baker et al.

*Primary Examiner*—Elli Peselev
*Attorney, Agent, or Firm*—Bierman, Muserlian and Lucas LLP

[57] ABSTRACT

An erythromycin compound of Formula I or its non-toxic acid addition salt having antibiotic activity.

19 Claims, No Drawings

ERYTHROMYCIN COMPOUNDS

OBJECTS OF THE INVENTION

It is an object of the invention to provide the novel erythromycin compounds of formula I and their non-toxic, pharmaceutically acceptable acid addition salts and a process and intermediates for their preparation.

It is another object of the invention to provide novel antibiotic compositions and a method of treating bacterial infections in warm-blooded animals.

These and other objects and advantages of the invention will become obvious from the following detailed description.

THE INVENTION

The novel compounds of the invention are compounds selected from the group consisting of a compound of the formula

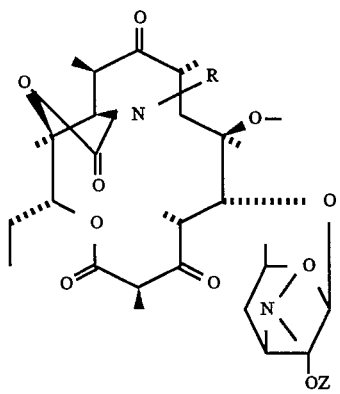

I wherein R is

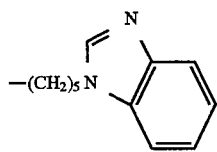

or —$(CH_2)_n$—Ar, n is an integer from 3 to 5, Ar is an optionally substituted heterocyclic selected from the group consisting of

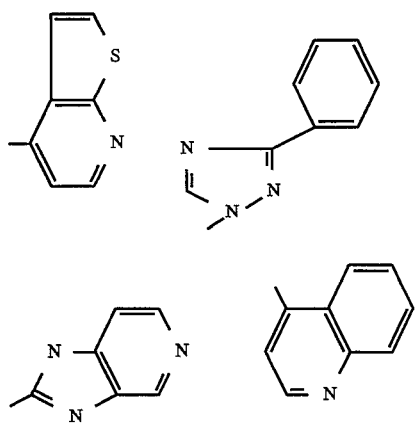

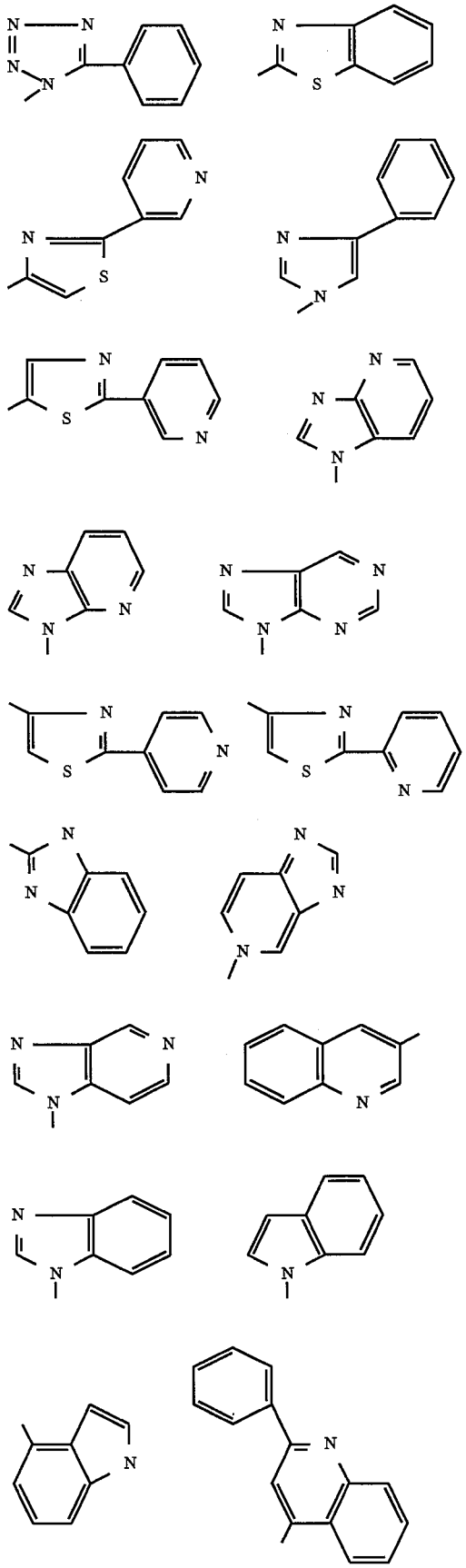

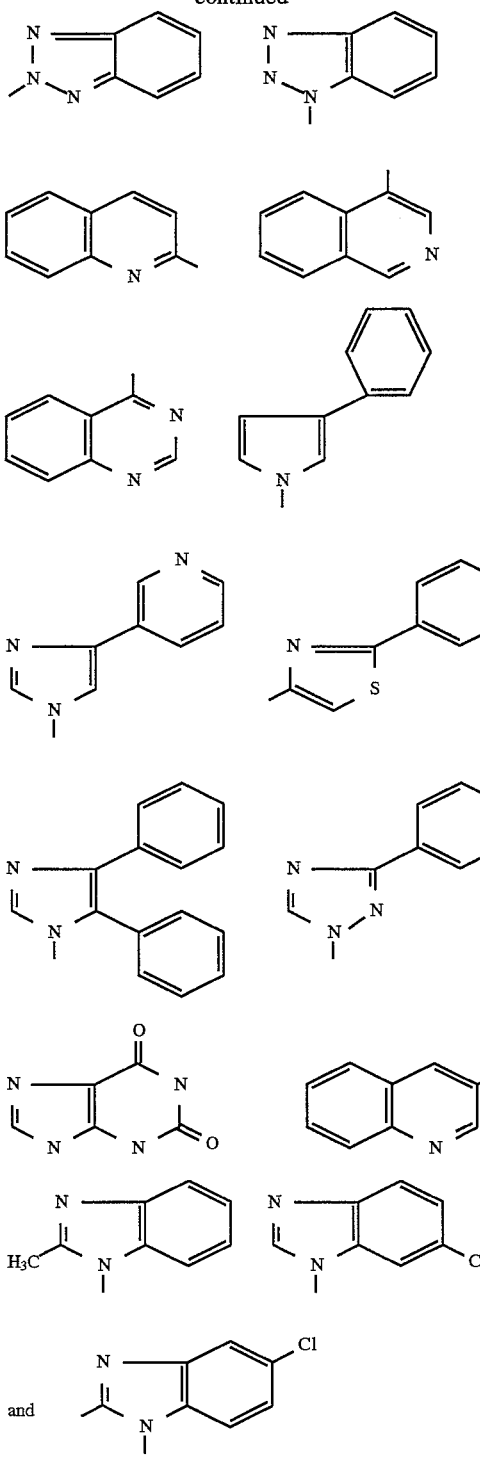

-continued

The heterocyclics may be substituted with at least one member of the group consisting of free, salified, esterified and amidified carboxyl, hydroxyl, halogen, —$NO_2$, —CN, alkyl, cycloalkyl, alkenyl, alkynyl, O-alkyl, O-alkenyl, O-alkynyl, S-alkyl, S-alkenyl, S-alkynyl, N-alkyl, N-alkenyl and N-alkynyl of up to 12 carbon atoms optionally substituted by one or more halogens,

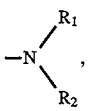

$R_1$ and $R_2$ are individually hydrogen or alkyl of up to 12 carbon atoms,

$R_3$ is alkyl of up to 12 carbon atoms, or an optionally substituted carbocyclic or heterocyclic aryl, O-aryl or S-aryl or heterocyclic aryl, O-aryl or S-aryl with one or more heteroatoms optionally substituted by one or more of the substituents mentioned above.

When the heterocyclic radical contains several rings linked together, or condensed, the substituent or substituents can be found on one and/or the other of the heterocyclic or carbocyclic rings. For example, if a heterocyclic nucleus is linked to or condensed with an aryl, the heterocyclic nucleus and the aryl nucleus can both carry one or more substituents.

The aryl is preferably phenyl or naphthyl. Examples of alkyl, alkenyl or alkynyl are preferably methyl, ethyl, propyl, isopropyl, n-butyl, isobutyl, terbutyl, decyl, dodecyl, vinyl, allyl, ethynyl, propynyl, propargyl, cyclobutyl, cyclopentyl or cyclohexyl. Halogen is preferably fluorine, chlorine or bromine and alkyl substituted by at least one halogen is preferably —$CHCl_2$, —$CHBr_2$, —$CHF_2$, —$CCl_3$, —$CBr_3$, —$CF_3$, —$CH_2CF_3$, —$CH_2CH_2CCl_3$ or —$CH_2CH_2CF_3$. The carboxylic acid remainder is preferably acetyl, propionyl, butyryl, isobutyryl, n-valeryl, isovaleryl, tert-valeryl and pivalyl.

Among the preferred compounds of formula I are those wherein Z is hydrogen, those wherein n is 4, those wherein Ar is the following optionally substituted

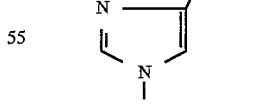

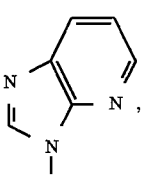

and Z is hydrogen or an acid remainder and their non-toxic, pharmaceutically acceptable acid addition salts.

Examples of suitable acids for the non-toxic, pharmaceutically acceptable acid addition salts are acetic acid, propionic acid, trifluoroacetic acid, maleic acid, tartaric acid, methane-sulfonic acid, benzenesulfonic acid, p-toluenesulfonic acid, hydrochloric acid, hydrobromic acid, hydroiodic acid, sulfuric acid, phosphoric and especially stearic acid, ethylsuccinic acid and laurylsulfuric acid.

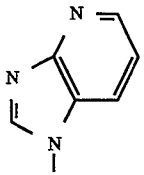

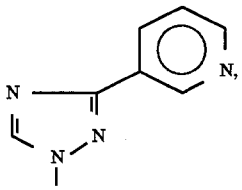

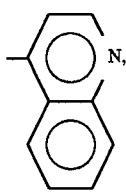

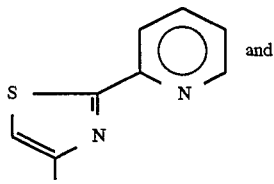 and

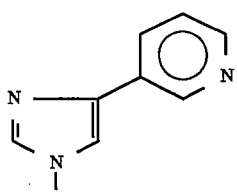

Specific preferred compounds of formula I are 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-phenyl-1H-imidazol-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(3H-imidazo(4,5-b)pyridin-3-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(1H-imidazo(4,5-b)pyridin-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(4-chlorophenyl)-1H-imidazol-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(2-methoxyphenyl)-1H-imidazol-1-yl)-butyl)-imino)]-erythromycin, 1,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(4-fluorophenyl)-1H-imidazol-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(7-methoxy-4-quinoleinyl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(2-(2-pyridinyl)-4-thiazolyl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(3-(3-pyridinyl)-1H-1,2,4-triazol-1-yl)-butyl)-imino)]-erythromycin, erythromycin and their non-toxic, pharmaceutically acceptable acid addition salts and most preferably 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(3-pyridinyl)-1H-imidazol-1-yl)-butyl)-imino)]-erythromycin.

The antibiotic compositions of the invention are comprised of an antibiotically effective amount of a compound of formula I and its non-toxic, pharmaceutically acceptable acid addition salts and an inert pharmaceutical carrier. The compositions may be in the form of tablets, dragees, capsules, granules, suppositories, ointments, creams, gels and injectable solutions or suspensions.

Examples of suitable pharmaceutical carriers or excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

These compositions can also be presented in the form of a powder intended to be dissolved extemporaneously in a suitable vehicle, for example apyrogenic sterile water.

The compositions possess a very good antibiotic activity on gram bacteria such as staphylococci, streptococci, pneumococci. They are useful in the treatment of infections caused by sensitive germs and particularly that of staphylococcia, such as staphylococcal speticemia, malignant staphylococcia of the face or skin, pyodermititis, septic or suppurating sores, boils, anthrax, phlegmons, erysipelas and acne, staphylococcia such as primary or post-influenzal acute anginas, bronchopneumonia, pulmonary suppurations, streptococcal infections such as acute anginas, otitis, sinusitis, scarlet fever, pneumococcal infections such as pneumonia, bronchitis; brucellosis, diphtheria, gonococcal infection.

The compositions of the invention are also active against infections caused by germs such as Haemophilus influenzae, Rickettsia, Mycoplasma pneumoniae, Chlamydia, Legionella, Ureaplasma, Toxoplasma or by germs of the Mycobaterium, Listeria, Meningococci and Campylobacter type. Particularly preferred are compositions using the compounds of Examples 1, 2, 3 and 29 to 35.

The novel method of the invention for treating bacterial infections in warm-blooded animals, including humans, comprises administering to warm-blooded animals an antibiotically effective amount of a compound of formula I or its non-toxic, pharmaceutically acceptable acid addition salts. The compounds may be administered buccally, rectally, parenterally or topically by application to the skin or mucous membrane. The usual daily dose is 0.6 to 4.0 mg/kg depending on the condition treated, the specific compound administered and the method of administration.

The novel process of the invention for the preparation of the compounds of formula I comprises reacting a compound of formula

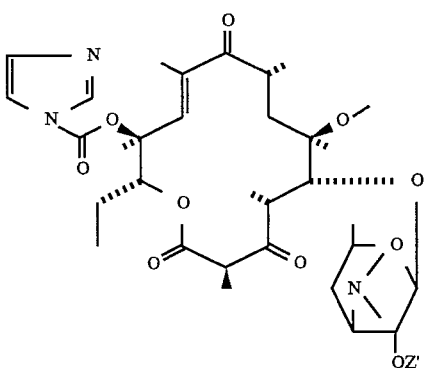

wherein Z' is the remainder of an organic carboxylic acid with a compound of the formula $$RNH_2 \quad \text{III}$$

wherein R has the above definition to form a compound of the formula

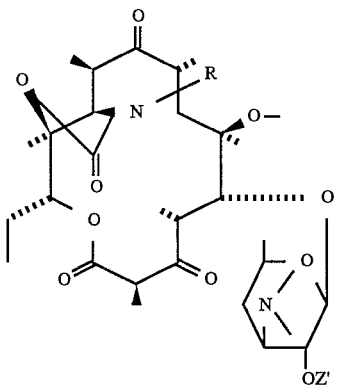

wherein R and Z' have the above definition, optionally subjecting the latter to the action of an agent releasing the Z' hydroxyl function and optionally reacting the latter with an acid to form the acid addition salt thereof.

The reaction of the compounds of the formulae II and III is effected in a solvent such as acetonitrile, dimethylformamide, tetrahydrofuran, dimethoxyethane or dimethylsulfoxide. The hydrolysis of the Z'-ester group is preferably effected with methanol or aqueous hydrochloric acid and the salification is effected by known procedures.

The compounds of formula II are described in European patent application No. 0,596,802. The new compounds of formula III may be prepared by the process described in J. Med. Chem. (1982), Vol. 25, p. 947 and subsequent, Tetrahedron Letters, Vol. 32,No. 14,pp. 1699–1702, (1991); J. Org. Chem., Vol. 54,No. 18,p. 4298–4301 (1989); J. Org. Chem. Vol. 28 No. 101, pp. 2589–2591 (1963) or the German Patent No. 3,406,416; J. Org. Chem., Vol. 6, pp. 895–901 (1941) or Synth. Commun., Vol. 17, No. 14, pp. 1741–1748 (1987).

Preferred compounds of formula III are
4-phenyl-1H-imidazole-1-butanamine,
3H-imidazo(4,5-b)-pyridine-3-butanamine,
1H-imidazo(4,5-b)-pyridine-3-butanamine,
2-phenyl-4-quinolinebutanamine,
1H-benzotriazole-1-butanamine,
2H-benzotriazole-2-butanamine,
1-methyl-1H-imidazo(4,5-c)-pyridine-2-butanamine,
3-methyl-3H-imidazo(4,5-c)-pyridine-2-butanamine,
5-chloro-1H-benzimidazole-1-butanamine,
7-methoxy-4-quinolinebutanamine,
1H-imidazo(4,5-c)-pyridine-1-butanamine,
9H-purine-9-butanamine,
1-methyl-1H-indole-4-butanamine,
3-phenyl-1H-1,2,4-triazole-1-butanamine-(hydrochloride),
5-phenyl-1H-tetrazole-1-butanamine-(hydrochloride),
2-benzothiazolebutanamine,
4-(thieno(2,3-b)-pyridine-4-yl-butanamine,
5,6-dimethyl-1H-benzimidazole-1-butanamine,
3-quinoleine-butanamine,
2-quinoleine-butanamine,
5H-imidazo-[4,5-c]-pyridine-5-butanamine,
1-methyl-1H-benzimidazol-2-butanamine,
6-chloro-1H-benzimidazol-2-butanamine,
2-methyl-1H-benzimidazol-2-butanamine,
4-(4-chlorophenyl)-1H-imidazol-1-butanamine,
2-(3-pyridinyl)-thiazol-5-butanamine,
7-methoxyquinoleine-4-butanamine,
4-(4-fluorophenyl)-1H-imidazol-1-butanamine,
4-(2-methoxyphenyl)-1H-imidazol-1-butanamine,
3-(3-pyridinyl)-1H-1,2,4-triazol-1-butanamine,
4-(3-pyridinyl)-1H-imidazol-1-butanamine,
2-(2-pyridinyl)-thiazol-4-butanamine,
2-phenylthiazol-4-butanamine,
4-(4-methoxyphenyl)-1H-imidazol-1-butanamine,
isoquinoleine-4-butanamine,
quinazoline-4-butanamine,
4,5-diphenyl-1H-imidazol-1-butanamine,
4-(3-methoxyphenyl)-1H-imidazol-1-butanamine,
4-(4-(trifluoromethoxy)-phenyl)-1H-imidazol-1-butanamine,
1,2,3,6-tetrahydro-1,3-dimethyl-2,6-dioxo-7H-purine-7-butanamine,
2-(4-pyridinyl)-thiazol-4-butanamine,
1H-indol-1-butanamine,
2-(3-pyridinyl)-thiazol-4-butanamine and their non-toxic, pharmaceutically acceptable acid addition salts.

In the following Examples, there are described several preferred embodiments to illustrate the invention. However, it is to be understood that the invention is not intended to be limited to the specific embodiments.

EXAMPLE 1

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-phenyl-1H-imidazol-1-yl)-butyl)-imino)])-erythromycin A mixture of 0.705 g of 11-déoxy-10,11-didéhydro-3-de-(2,6-didéoxy-3-C-méthyl-3-O-méthyl-α-L-ribohexopyranosyl)-oxy)-12-O-((1H-imidazol-1-yl)-carbonyl)-6-O-méthyl-3-oxo-érythromycine-2'-acétate obtained as indicated in example 1C of European Patent application 0,596,802, 3 ml of acetonitrile with 10% water and 1.08 g of 4-(4-phenyl-1H-imidazol-1-yl)-butanamine was taken to 63° C. and the reaction mixture was maintained at this temperature for 5 hours and then left to return to ambient temperature. The reaction mixture was poured into a solution of sodium acid phosphate and extraction was carried out with ethyl acetate. The organic phases were washed with water, dried, filtered and concentrated to obtain 1.5 g of a product to which 210 ml of methanol were added. The mixture was stirred for 16 hours under a nitrogen atmosphere and at ambient temperature. After concentration, 1.4 g of product were obtained which was purified by chromatography on silica, eluant $CH_2Cl_2$-MeOH-$NH_4OH$ (93-7-0.4) to obtain after concentration 0.305 g of the crude desired product which was crystallized from isopropyl ether, followed by washing and drying at 50° C. under reduced pressure to obtain 0.267 g of the desired product melting at 222°C.–231° C. and having a specific rotation of $[\alpha]_D=+18°$ (C.=0.9% in $CHCl_3$).

NMR $CDCl_3$ ppm 0.84 (t): $CH_3$-$CH_2$; 1.01 (d)–1.17 (d)–1.24 (d): the $CH_3$-CH's; 1.30 (d)–1.38 (d)–1.34 to 1.47:6 and 12-Me; 2.27 (s): $N(Me)_2$; 2.45 (–): H'3; 2.61 (m): $H_8$; 2.63 (s): 6-OMe; 3.04 (–): $H_4$; 3.13 (q): $H_{10}$; 3.18 (dd): H'$_2$; 3.53 (–): H'$_5$; 3.56 (s): $H_{11}$; 3.67 (–)–3.75 (–): the

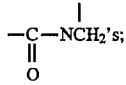

3.87 (q): $H_2$; 3.99 (t): $CH_2NC$; 4.23 (d): $H_5$; 4.27 (d): H'$_1$; 4.94 (dd): $H_{13}$; 7.26 (s): H"$_5$; 7.5 (s): H"$_2$; 7.20:H in para position; 7.35: H in meta position; 7.76: H in ortho position.

PREPARATION 1: 4-(4-phenyl-1H-imidazol-1-yl)-butanamine

Stage A: 2-(4-(4-phenyl-1H-imidazol-1-yl)-butyl-1H-iso-indole-1,3(2H)dione

A solution of 5.05 g of 4-phenyl-1H-imidazole in 25 ml of DMF was introduced dropwise over 90 minutes into a mixture of 7 ml of DMF dried on siliporite and 2.02 g of sodium hydride and then, 10.86 g of 2-(4-bromobutyl)-1H-iso-indole-1,3(2H)dione-N-4-bromobutylphthalimide in solution in 25 ml of DMF were introduced. The solution was taken to 70° C. for about 90 minutes and was then allowed to return to ambient temperature. The solution was concentrated, taken up in water and extracted with ethyl acetate. The organic phases were washed with water, dried, filtered and concentrated to obtain 15 g of product which was crystallized from ethyl acetate. The product was separated off, washed with ethyl acetate and dried under reduced pressure at 50° C. to obtain 5.5 g of the desired product melting at 130°–132° C.

NMR $CDCl_3$ ppm 1.75 (m) (2H)–1.86 (m) (2H): central $CH_2$'s; 3.74 (t): 2H; 4.03: 2H; 7.22 (t): 2H $H_4$; 7.26 (m): 1H H'$_3$; 7.36 (t): 2H $H_3$ and $H_5$; 7.56 (d): H'$_5$; approx. 7.73 (m): 4H; approx. 7.86 (m): $H_2$ and $H_6$.

Stage B: 4-(4-phenyl-1H-imidazol-1-yl)-butanamine

A mixture of 3.45 g of the product of Stage A, 100 ml of ethanol and 0.97 ml of hydrazine hydrate was refluxed for 8 hours and the reaction mixture was then concentrated. About 50 ml of 2N sodium hydroxide were added and extraction was carried out with ethyl acetate. The organic phases were washed with 2N sodium hydroxide, then with sodium chloride. After drying, filtering and concentrating, 2.21 g of the desired product were obtained.

NMR $CDCl_3$ ppm 1.47 (m)–1.87 (m): central $CH_2$'s; 2.73 (t)–3.97: —$CH_2$—$NH_2$; 7.20(d): H'$_3$; 7.50 (d): H'$_5$; 7.37 (wt) 2H: $H_3$ $H_5$; 7.24 (it) 1H: $H_4$; 7.77 (m) 2H: $H_2$ and $H_6$.

EXAMPLE 2

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(3H-imidazo (4,5-b)-pyridin-3-yl)-butyl)-iraino)]-erythromycin 708.2 mg of 11-deoxy-10,11-didehydro-3-de(2,6-dideoxy-3-C-methyl-3-O- methyl-α-L-ribohexopyranosyl)-oxy)-12-O-((1H-imidazol-1-yl)-carbonyl)-6-O-m ethyl-3-oxo-erythroraycine-2'-acetate obtained as Example 1C of European Patent application 0,596,802, and 958 mg of 3H-imidazo(4,5-b)-pyridin-3-butanamine were dissolved in 2.82 ml of acetonitrile and 0.28 ml of water. The reaction mixture was heated to 80° C. and was then allowed to return to ambient temperature and was poured into a solution of sodium acid phosphate. Extraction was carried out with methylene chloride followed by washing with water. The aqueous phases were collected and extraction was carried out again. After drying, filtering and rinsing, 826 mg of product were obtained which was dissolved in 16.5 ml of methanol. The reaction solution was stirred at ambient temperature for 20 hours to obtain 789 g of crude desired product which was purified by chromatography, eluting with a mixture of methylene chloride, methanol and ammoniura hydroxide (94-6-0.4) to obtain 327 mg of the desired product melting at 200° C. and having a specific rotation $[\alpha]_D=+13°$ (C=1% in $CHCl_3$).

NMR $CDCl_3$ 400 MHz ppm 0.85 (t): $CH_3$—$CH_2$; 1.01 (d)–1.16 (d)–1.25 (d)–1.30 (d)–1.26 (d): the $CH_3$—CH's; 1.35 and 1.47: 6 and 12 Me; approx. 1.63 and approx. 1.98: the central $CH_2$'s of the chain; 2.27 (s): $N(CH_3)_2$; 2.46 (m): H'$_3$; approx. 2.59 (m): $H_8$; 2.61 (s): 6-OMe; 3.07 (m): $H_4$; 3.12 (wq): $H_{10}$; 3.18 (dd): H'$_2$; 3.54 (m): H'$_5$; 3.57 (s): $H_{11}$; 3.6 to 3.8:

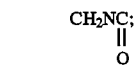

3.85 (q): $H_2$; 4.24 (d): $H_5$; 4.29 (d): H'$_1$; approx. 4.35 (m): $CH_2NC$=; 4.93 (dd): $H_{13}$; 7.21 (dd): $H_6$ aromatic; 8.04 (dd): $H_7$ aromatic; 8.11 (s): $H_2$ aromatic; 8.38 (dd): $H_5$ aromatic.

EXAMPLE 3

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(1H-imidazo(4,5-b)-pyridin-1-yl)-butyl)-imino)]-erythromycin 708.3 mg of 11-deoxy-10,11-didehydro-3-de(2,6-dideoxy-3-C-methyl-3-O-methyl-α-L-ribohexopyranosyl)-oxy)-12-O-((1H-imidazol-1-yl)-carbonyl)-6-O-methyl-3-oxo-érythromycin-2'-acétate obtained as in Example 1C of the European Patent application 0,596,802, were added to a solution of 953 mg of 1H-imidazo(4,5-b)-pyridine-3-butanamine, 2.82 ml of acetonitrile and 0.28 ml of water and the reaction mixture was taken to 55° C. and maintained at this temperature for 44 hours. 0.5 ml of acetonitrile were added and the mixture was maintained at 55° C. for a further 20 hours. It was allowed to return to ambient temperature and was poured into a saturated solution of sodium acid phosphate. The aqueous phase was extracted with methylene chloride and the chloromethylene phases were washed with water. Drying over sodium sulfate was carried out, followed by filtration and evaporation to obtain 806 mg of product to which 16.1 ml of methanol were added. The reaction mixture was maintained at ambient temperature for 24 hours and evaporated to dryness to obtain 656 mg of a product which was chromatographed on silica, eluting with a $CH_2Cl_2$-MeOH-$NH_3$ mixture (94-6-0.4). The crude desired product was obtained which was purified by chromatography on silica, eluting with a $CHCl_3$-MeOH-$NH_4OH$ mixture (94-6-0.4). The residue was dissolved in an ethyl acetate—isopropyl ether mixture, followed by filtration and evaporation to dryness to obtain the desired product melting at 203° C. and having a specific rotation of $[\alpha]_D = 17.6°$ (C=1% in CHCl$_3$).

0.81 (t): CH$_3$—CH$_2$; 1.00 (d)–1.17 (d)–1.25 (d)–1.31 (d)–1.38 (d): the CH$_3$—CH's; 1.35 (s)–1.47 (s): 6 and 12-CH$_3$; 1.68 (m) and 1.93 (m): the central CH$_2$'s of the chain; 2.27 (s): N(CH$_3$)$_2$; 2.61 (s): 6-OCH$_3$; 2.45 (m): H'$_3$; approx. 2.60 (m in masked part): H$_8$; 3.07 (m): H$_4$; approx. 3.15 (wq): H$_{10}$; 3.18 (dd): H'$_2$; 3.56 (s): H$_{11}$; 3.53 (m): H'$_5$; 3.60 to 3.80 (m): CO—N—CH$_2$; 3.87 (q): H$_2$; approx. 4.25 (m): CH$_2$—N—C=; 4.24 (d): H$_5$; 4.28 (d): H'$_1$; 4.91 (dd): H$_{13}$; 7.21 (dd, J=5 and 8): H$_6$; 7.80 (dd, J=8 and 1.5): aromatic H$_7$'s; 8.56 (dd, J=5 and 1.5): H$_5$; 8.15 (s): H$_2$+CH$_2$Cl$_2$.

PREPARATION 2: Preparation of the starting products of Examples 2 and 3

3H-imidazo(4,5-b)pyridine-3-butanamine and 1H-imidazo(4,5-b)-pyridine-1-butanamine Stage A:

10.3 g of potassium carbonate were added to a solution of 5.95 g of 4-azabenzimidazole and 15.5 g of N-4-bromobutyl-phthalimide in 30 ml of dimethylformamide and the mixture was stirred for 20 hours at ambient temperature. The insoluble part was filtered off and rinsed with methylene chloride. The organic phase was washed with water, then dried over magnesium sulfate and evaporated. The oily residue obtained was washed with petroleum ether, then with isopropyl ether to obtain 16.3 g of a yellow solid which was purified by chromatography on silica, eluting with a methylene chloride—acetone mixture to obtain 4.9 g of product (A) melting at 143° C., and 3.9 g of product (B) melting at 172° C.

Stage B1: 3H-imidazo(4,5-b)-pyridine-3-butanamine (starting product of Example 2)

A mixture of 32.86 g of product (A) of the previous stage, 697 ml of ethanol and 20 ml of hydrazine was refluxed for 19 hours and then, the mixture was allowed to return to ambient temperature, filtered, rinsed and evaporated to dryness. The residue was taken up in methylene chloride, filtered, rinsed and evaporated to dryness to obtain 18.87 g of the desired product.

NMR CDCl$_3$—250 MHz 1.52 (m)–2.00 (m): 2 central CH$_2$'s; 1.63 (wide s): 2 mobile H's; 2.76 (t): CH$_2$—CH$_2$—NH$_2$; 4.33 (t):

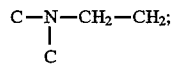

7.24 (dd, J=8 and 5): H$_6$; s 8.08 (dd, J=8 and 1.5): H$_7$; 8.40 (dd, J=5 and 1.5): H$_5$; 8.08 (s): H$_2$.

Stage B2: 1H-imidazo(4,5-b)-pyridine-1-butanamine (starting product of Example 3)

A mixture of 32 g of product (B) of Preparation 3, 640 ml of ethanol and 24.8 ml of hydrazine was refluxed for 21 hours and then, the mixture was allowed to return to ambient temperature. Filtration was carried out, followed by rinsing with ethanol and evaporating under reduced pressure. The residue was taken up in methylene chloride, followed by filtration, rinsing and evaporating to dryness to obtain 19.5 g of the desired product.

NMR CDCl$_3$ 1.45 (m)–1.96 (m): 2 central CH$_2$'s; 2.74 (t): CH$_2$—NH$_2$; approx. 1.45 (m): mobile; 4.23 (t):

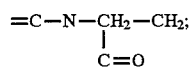

7.24 (dd, J=8 and 5): H$_6$; 7.75 (dd, J=8 and 1.5): H$_7$; 8.58 (dd, J=5 and 1.5): H$_5$; 8.13 (s): H$_2$+EtOH.

Operating as previously, the following products were obtained:

EXAMPLE 4

11,12-dideoxy-3-de-[(2,6-dideoxy-3-O-methyl-3-O-methyl-α-L-ribohexoyranosyl)-oxy)-6-O-methyl-3-oxo-12,11-(oxycarbonyl)-((4-(thieno(2,3-b)-pyridin-4-yl)-butyl)-imino)]-erythromycin melting at 176°–178°C. and having a specific rotation of $[\alpha]_D$=+17° C. (C=0.9% in CHCl$_3$).

EXAMPLE 5

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(3-phenyl-1H-1,2,4-triazol-1-yl)-butyl)-imino)]-erythromycin melting at 208°–210° C. and having a specific rotation of $[\alpha]_D$=+17° (C=1% in CHCl$_3$).

EXAMPLE 6

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(1-methyl-1H-imidazo(4,5-c)pyridin-2-yl)-butyl)-imino)]-erythromycin and having a specific rotation of $[\alpha]_D$=+19° (C=1% in CHCl$_3$).

EXAMPLE 7

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(3-methyl-3H-imidazo(4,5-c)pyridin-2-yl)-butyl)-imino)]-erythromycin and having a specific rotation of $[\alpha]_D$=+16° (C=1% in CHCl$_3$).

EXAMPLE 8

11,12-dideoxy-3-de-[(2,6-dideoxy-3-C-methyl-3-O-methyl-α-L-ribohexopyranosyl)-oxy)-6-O-methyl-3-oxo-12,11-methyl-((4-(7-methoxy-4-quinolinyl)-butyl)-imino)]-erythromycin and having a specific rotation of $[\alpha]_D$=+15.8° (C=1% in CHCl$_3$).

EXAMPLE 9

11,12-dideoxy-3-de((2,6-dideoxy-3-C-methyl-3-O-methyl-α-L-ribohexopyranosyl)-oxy)-6-O-methyl-3-oxo-12,11-(oxycarbonyl -((4-(5-phenyl-1H-tetrazol-1-yl)-butyl) -imino)]-erythromycin melting at 132°–134° C. and having a specific rotation of $[\alpha]_D$=+25° (C=1% in CHCl$_3$).

EXAMPLE 10

11,12-dideoxy-3-de((2,6-dideoxy-3-C-methyl-3-O-methyl-α-L-ribohexopyranosyl)-oxy)-6-O-methyl-3-oxo-12,11-(oxycarbonyl-(( 4-(2-benzothiazolyl)-butyl)-imino)]-erythromycin melting at 179°–181° C. and having a specific rotation of $[\alpha]_D$=+18° (C=1% in CHCl$_3$).

EXAMPLE 11

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl -((4-(2-(3-pyridinyl)-4-thiazolyl)-butyl) -imino)]-erythromycin melting at 150°–152° C. and having a specific rotation of $[\alpha]_D$=+17° (C=0.9% in CHCl$_3$).

EXAMPLE 12

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(2-(3-pyridinyl)-5-thiazolyl)-butyl)-imino)]-erythromycin melting at 155°–159° C. and having a specific rotation of $[\alpha]_D=+12°$ (C=1% in CHCl$_3$).

EXAMPLE 13

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(9H-purin-9-yl)-butyl)-imino)]-erythromycin.

EXAMPLE 14

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(1H-imidazo(4,5-c)-pyridin-1-yl)-butyl)-imino)]-erythromycin with a $R_f=0.42$ (CHCl$_3$+8% of MeOH with 8% of NH$_4$OH).

EXAMPLE 15

11,12-dideoxy-3-de-((2,6-dideoxy-3-C-methyl-3-O-methyl-α-L-ribohexopyranosyl)-oxy)-6-O-methyl-3-oxo-12,11-(oxycarbonyl-((5-(1H-benzimidazol-1-yl)-pentyl)-imino)]-erythromycin. Prepared from 2-(4-bromophenyl) 1H-iso-indole 1,3 (2H)-dione.

EXAMPLE 16

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((5-chloro-1H-benzimidazol-1-yl)-butyl)-imino)]-erythromycin melting at 145°–148° C.

EXAMPLE 17

11,12-dideoxy-3-de-[(2,6-dideoxy-3-C-methyl-3-O-methyl-α-L-ribohexopyranosyl)-oxy)-6-O-methyl-12,11-(oxycarbonyl-((4-(1H-indol-1-yl)-butyl)-imino)]-erythromycin.

EXAMPLE 18

11,12-dideoxy-3-de-[(2,6-dideoxy-3-C-methyl-3-O-methyl-α-L-ribohexopyranosyl)-oxy)-6-O-methyl-12,11-(oxycarbonyl-((4-(1-methyl-1H-indol-4-yl)-butyl)-imino)]-erythromycin and having a specific rotation of $[\alpha]_d=20°$, (c=1% in CHCl$_3$).

EXAMPLE 19

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(2-phenyl-4-quinolinyl)-butyl)-imino)]-erythromycin melting at 195°–197° C.

EXAMPLE 20

11,12-dideoxy-3-de-((2,6-dideoxy-3-C-methyl-3-O-methyl-α-L-ribohexopyranosyl)-oxy)-6-O-methyl-3-oxo-12,11-(oxycarbonyl-((4-(1H-benzotriazole-1-yl)-butyl)-imino)]-erythromycin melting at 200°–202° C.

EXAMPLE 21

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(2H-benzotriazol-2-yl)-butyl)-imino)]-erythromycin melting at 164°–166° C.

EXAMPLE 22

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(5,6-dimethyl-1H-benzimidazol-1-yl)-butyl)-imino)]-erythromycin melting at 174°–176° C.

EXAMPLE 23

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(3-quinolinyl)-butyl)-imino)]-erythromycin melting at 195°–197° C.

EXAMPLE 24

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(2-quinolinyl)-butyl)-imino)]-erythromycin melting at 179°–181° C.

EXAMPLE 25

11,12-dideoxy-3-de-[(2,6-dideoxy-3-C-methyl-3-O-methyl-α-L-ribohexopyranosyl)oxy)6-O-methyl 3-oxo 12,11-(oxycarbonyl-((4-(2-methyl-1H-benzimidazol-1-yl)-butyl)-imino)]-erythromycin melting at 128°–132° C.

EXAMPLE 26

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(6-chloro-1H-benzimidazol-1-yl)-butyl)-imino)]-erythromycin melting at 192°–194° C.

EXAMPLE 27

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(1-methyl-1H-benzimidazol-2-yl)-butyl)-imino)]-erythromycin

EXAMPLE 28

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(5H-imidazo (4,5-c)pyridin-5-yl)-imino)]-erythromycin with a specific rotation of $[\alpha]_D=12.20°$ (C=1% in CHCl$_3$).

EXAMPLE 29

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(4-chlorophenyl)-1H-imidazol-1-yl)-butyl)-imino)]-erythromycin 1 g of 11-deoxy-10,11-didehydro-3-de(2,6-dideoxy-3-C-methyl 3-O-methyl-α-L-ribohexopyranosyl)-oxy)-12-O-((1H-imidazol-1-yl)-carbonyl)-6-O-methyl-3-oxo-erythromycin 2'-acetate prepared as in Example 1C of the European Patent Application EP 0,596,802 was heated for 7 hours at 75° C. in 4 ml of acetonitrile with 10% water with 1.4 g of 4-(4-(4-chlorophenyl)-1H-imidazol)-butanamine. The reaction medium was allowed to return to ambient temperature and was diluted with water. Extraction was carried out with ethyl acetate, followed by drying. The solvent was evaporated to obtain 2.3 g of product acetylated in position 2'. 60 ml of methanol were added and the mixture was stirred for 16 hours. The solvent was evaporated and the residue was chromatographed on silica (eluant: CH$_2$Cl$_2$-

MeOH-NH₄OH 95-5-0.4), followed by concentration. The residue was crystallized from ether and the crystallized product was dried under reduced pressure at 80° C. to obtain 381 mg of the expected product melting at 192°–194° C.

NMR CDCl₃ ppm 0.83 (t): $\underline{CH_3}$—CH₂; 1.00 (d)–1.16 (d)–1.24 (d)–1.30 (d)–1.38 (d): the $\underline{CH_3}$—CH's; 1.33 (s)–1.47 (s): 6 and 12 Me; 2.26 (s): N(Me)₂; 2.44 (m): H'₃; 2.61 (s): 6—OMe; 2.60 (m): H₈; 3 00 to 3 21: H₄, H₁₀ and H'₂; 3.55 (m): H'₅; 3.56 (s): H₁₁; 3.60 to 3.80 2H–3.99 (t) 2H: CH₂NC=; 3.87 (q): H₂; 4.23 (d): H₅; 4.28 (d): H'₁; 4.93 (dd): H₁₃; 7.26 (d): H₅ imidazole; 7.50 (d): H₂ imidazole; 7.32–7.70: aromatics; 3.51: OH.

Preparation of 4-(4-chlorophenyl)-1H-imidazole-1-butanamine

Stage A: 4-(4-chlorophenyl)-1H-imidazole.

EXAMPLE 30

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(2-methoxyphenyl)-1H-imidazol-1-yl)-butyl)-imino)]-erythromycin 706 mg of the starting compound of Example 29 (obtained as in Example 1C of the European Patent Application EP 0,596,802) in 3 ml of acetonitrile and 908 mg of 4-(4-(2-methoxyphenyl)-1H-imidazol-1-yl)-butanamine were heated at 80° C. for 8 hours and then the reaction medium was allowed to return to ambient temperature and was poured into a solution of sodium hydrogen phosphate (0.5M). Extraction was carried out with ethyl acetate and the extracts were washed with water and dried. The solvent was evaporated to obtain 1.6 g of product acetylated in position 2'. 50 ml of methanol were added and the mixture was stirred for 16 hours. The solvent was evaporated and the residue was chromatographed on silica (eluant: AcOEt-TEA at 4%) and crystallized from ether to obtain 194 mg of the expected product melting at 143°–145° C.

NMR CDCl₃ ppm 0.85 (t): $\underline{CH_3}$—CH₂; 1.01 (d)–1.16 (d)–1.24 (d)–1.30 (d)–1.37 (d): the $\underline{CH_3}$—CH's; 1.34 (s)–1.47 (s): 6 and 12 Me; 2.26 (s): N(Me)₂; 2.44 (m): H'₃; 2 60 (m): H₈; 2 64 (s): 6-OMe; 3 08 (m): H₄; 3.12 (wq): H₁₀; 3.17 (dd): H'₂; 3.54 (m): H'₅; 3.57 (s): H₁₁; 3.66 (m)–3.74 (m):

3.85 (q): H₂; 3.95 (s): Φ-OMe; 3.99 (wq): CH₂—N—C=; 4.24 (d): H₅; 4 27 (d): H'₁; 4.93 (dd): H₁₃; 6.97 (wd): H₆; 7.51 (s): the imidazole H's; 7.02: phenyl H₆; 7.19 (ddd) phenyl H₄ and H₅; 8.19 (dd): H₂.

Preparation of 4-(2-methoxyphenyl)-1H-imidazol-1-butanamine

Stage A: 4-(2-methoxyphenyl)-1H-imidazole.

9.36 g of 2-bromo-2'-methoxyacetophenone in 50 ml of formamide were refluxed and then the reaction medium was allowed to return to ambient temperature and was washed with a 2N hydrochloric acid solution, followed by filtration and alkalinizing to pH 8–9 using 2N sodium hydroxide. Extraction was effected with dichloromethane and the extracts were washed with water, dried and evaporated to dryness. The residue was chromatographed on silica (eluant: CH₂Cl₂-MeOH-NH₄OH 95-5-0.4) to obtain 6.15 g of the expected product.

Stage B: 2-(4-(4-(2-methoxyphenyl)-1H-imidazol-1-yl)-butyl-1H-iso indol-1,3(2H)-dione.

Using the procedure of Stage A of Example 1, 6 g of the product of Stage A, 1.99 g of sodium hydride and 9.93 g of N-4-bromobutyl phthalimide were reacted to obtain 6.15 g of the expected product.

Stage C: 4-(2-methoxyphenyl)-1H-imidazol-1-butanamine(fumarate).

Using the procedure of Stage B of Example 1, 5.65 g of the product of Stage B and 1.45 ml of hydrazine hydrate in 75 ml of ethanol were reacted to obtain 3.8 g of crude product which was dissolved in 4 ml of tetrahydrofuran. Then, 1.87 g of fumaric acid in solution in 20 ml of methanol were added and 10 ml of ether were added. The crystals formed were separated and dried at 80° C. under 23.34 g of bromo 4-chloro acetophenone in 150 ml of formamide was refluxed for one hour and the reaction medium was allowed to cool and alkalinized with a sodium hydroxide solution. Extraction was carried out with dichloromethane and the extracts were washed with water and dried. The solvent was evaporated and the residue was chromatographed on silica (eluant: CH₂Cl₂—MeOH—NH₄OH 8-2-0.04) to obtain 13.4 g of the expected product melting at 146°–148° C.

Stage B: 2-(4-(4-(4-chlorophenyl)-1H-imidazol-1-yl) butyl)-1H-iso indol-1,3(2H)-dione.

Using the procedure of Stage A of Example 1, 12.2 g of the product of Stage A, 4.96 g of sodium hydride and 23.83 g of N-4-bromobutyl-phthalamide were reacted to obtain 9.7 g of the expected product.

Stage C: 4-(4-chlorophenyl)-1H-imidazol-1-butanamine.

Using the procedure of Stage B of Example 1, 14.2 g of product of Stage B and 3.6 ml of hydrazine hydrate in 200 ml of ethanol were reacted to obtain 12 g of crude product which was chromato-graphed on silica (eluant CH₂Cl₂-MeOH-NH₄OH 8-2-0.04) to obtain the expected product, which is used as is for the synthesis.

NMR (CDCl₃) ppm 1.22 (ws): mobile 2H's; 1.47 (m)–1.88 (m): 2 central CH₂'s; 2.74 (m): CH₂—$\underline{CH_2}$—N; 3.98 (m):

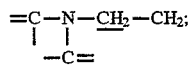

7.19 (d, J=1.5)–7.50 (d, J=1.5): H₂ and H₅; 7.33 and 7.70: aromatics. reduced pressure to obtain 3.77 g of the fumarate of the expected product melting at 160°–162° C.

NMR (CDCl₃) ppm 1.48 (m) 2H-1.87 (m) 2H: the central CH₂'s; 3.46: NH₂ ; 2.73 (t): CH₂N; 3.94 (s): Φ—OMe; 3.97 (t):

6.94 (dd): H₆; 7.04 (dt)–7.21 (ddd): H₅ and H₄; 7.51: H'₂ and H'₅; 8.19 (dd): H₂.

EXAMPLE 31

11,12-dideoxy-3-de-[(2,6-dideoxy-3-C-methyl-3-O-methyl-α-L-ribohexopyranosyl)-oxy)-6-O-methyl-oxo-12,11-(oxycarbonyl-((4-(4-(4-fluorophenyl)-1H-imidazol-1-yl)-butyl) imino)]-erythromycin 2.11 g of the starting compound of Example 29 (obtained as in Example 1C of the European Patent Application EP 0,596,802) in 9 ml of acetonitrile and 2.8 g of 4-(4-(4- fluorophenyl)-1H-imidazol-1-yl)-butanamine were heated at 60° C. for 4 hours 30 minutes. The reaction medium was allowed to return to ambient temperature and was poured into water. Extraction was carried out with ethyl acetate and the extracts are washed with water and dried. The solvent was evaporated to obtain 5.2 g of product acetylated in position 2'. 20 ml of methanol were added to it and the mixture was stirred for 3 hours 30 minutes. The solvent was evaporated and the residue was chromatographed on silica (eluant: CH$_2$Cl$_2$-MeOH-NH$_4$OH 95-5-0.3). Crystallization from ether was carried out to obtain 1.34 g of the expected product melting at 190°–192° C.
NMR CDCl$_3$ ppm
1.33 (s)–1.47 (s): 6 and 12 Me; 2.27 (s): N(Me)$_2$ ; 2.61 (s): 6-OMe; 3.0 to 3.18: H$_4$ and H$_{10}$; 3.56 (s): H$_{11}$; 3.59 to 3.81:

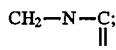

3.98 (t):

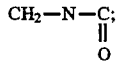

approx. 7.05—approx. 7.73: fluorophenyl; 7.21 (d): H$_5$ imidazole; 7.49 (d): imidazole H$_2$.

Preparation of 4-(4-fluorophenyl)-1H-imidazol-1-butanamine

Stage A: 4-(4-fluorophenyl)-1H-imidazole.

10.85 g of 4-fluorophenacyl bromide in 60 ml of formamide were refluxed for 2 hours and the reaction medium was allowed to return to ambient temperature and was acidified to pH 2 using N hydrochloric acid, followed by filtration. After neutralizing by the addition of ammonium hydroxide, extraction with dichloromethane was effected and the organic phase was washed with water and dried. The solvent was evaporated and the residue was chromatographed on silica (eluant: CH$_2$Cl$_2$-MeOH-NH$_4$OH 95-5-0.4) to obtain 5.8 g of the expected product melting at 130°–132° C.

Stage B: 2-(4-(4-(4-fluorophenyl)-1H-imidazol-1-yl)-butyl-1H-iso indol-1,3(2H)-dione.

Using the procedure of Stage A of Example 1, 10 g of the product of Stage A, 1.95 g of sodium hydride and 11.80 g of N-4-bromobutyl-phthalamide were reacted to obtain 7.53 g of the expected product melting at 138°–140° C.

Stage c: 4-(4-fluorophenyl)-1H-imidazol-1-butanamine.

Using the procedure of Stage B of Example 1, 3.64 g of the product of Stage B and 1 ml of hydrazine hydrate in 80 ml of ethanol were reacted to obtain 2.4 g of crude product which was chromatographed on silica (eluant: CH$_2$Cl$_2$-MeOH-NH$_4$OH 8-2-0.03) to obtain the desired product which was used as is for the synthesis.
NMR (CDCl$_3$) ppm
1.48 (m)-1.81 (m): the central CH$_2$'s; 2.74 (t): N—CH$_3$; 3.98 (t): >N—CH$_2$—CH$_2$; 7.06 (t): >CH—F; 7.22 (m):

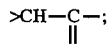

7.49 (s): imidazole H$_2$; 7.15 (s): imidazole H$_5$.

EXAMPLE 32

11,12-dideoxy-3-de-[(2,6-dideoxy-3-C-methyl-3-O-methyl-α-L-ribohexopyranosyl)-oxy)-6-O-methyl-3-oxo-12,11-oxycarbonyl-((4-(7-methoxy-(4-quinolinyl)-butyl)-imino)]-erythromycin 706 mg of the starting compound of Example 29 (obtained as in Example 1C of the European Patent Application EP 0,596,802) in 4 ml of acetonitrile and 1.43 g of 4-(4-7-methoxy-4-quinolinyl)-butanamine were heated at 50° C. for 53 hours. The reaction medium was allowed to return to ambient temperature and was poured into a solution of sodium hydrogen phosphate (0.5M). Extraction was carried out with dichloromethane and the extracts were washed with water and dried. The solvent was evaporated to obtain 1.09 g of product acetylated in position 2'. 10 ml of methanol were added to it and the mixture was stirred for 16 hours. The solvent was evaporated and the residue was chromatographed on silica (eluant: CH$_2$Cl$_2$-MeOH 95-5). Crystallization from ether was carried out to obtain 295 mg of the expected product melting at 110° C.
NMR CDCl$_3$ ppm
3.06 (m): —(CH$_2$)$_2$—CH<; 3.70 (m): —N—CH$_2$—; 3.95 (s): —OCH$_3$; 7.12 (d)–7.19 (dd)–7.42 (d)–7.94 (d)–8.70 (d): pyridine.

Preparation of 7-methoxy-quinoline-4-butanamine

Stage A: triphenyl phosphonium salt of N-(3-bromopropyl)-phthalimide.

13.4 g of N-bromopropyl-phthalimide and 13.15 g of triphenylphosphine suspended in 75 ml of xylene were refluxed for 44 hours and the reaction medium was allowed to return to ambient temperature. The precipitate was separated, washed with ethyl ether and dried under reduced pressure at 60° C. to obtain 24.88 g of the expected product melting at 220°–222° C.

Stage B: Z-(2-(4-(7-methoxyquinolinyl)-3-butenyl-1H-isoindol-1,3(2H)-dione.

4 g of 7-methoxy-4-quinolinylcarboxaldehyde were added to a suspension of 12.47 g of the triphenylphosphonium salt of 3-bromopropyl-phthalimide in 200 ml of tetrahydrofuran and after the reaction medium was cooled to −50° C., 2.72 g of potassium terbutylate were added. The temperature was allowed to rise slowly to −6° C., followed by filtration. The filtrate was concentrated, the residue is taken up in ethyl acetate, washed with water and dried. The solvent was evaporated to obtain 9.26 g of crude product which was chromatographed on silica (eluant: CHCl$_3$— AcOEt 80-20, then 70-30) to obtain 3.575 g of the expected product.

Stage C: 2-(4-(7-methoxy-4-quinolinyl)-butyl)-1H-isoindol-1,3(2H)-dione.

3.50 g of the product of Stage B were dissolved in 50 ml of methanol and 0.36 g of palladium on activated charcoal were added. The mixture was hydrogenated for 3 hours under 600 mbars. Filtration was carried out and the solvent was evaporated to obtain 3.48 g of the expected product.

Stage D: 7-methoxy-quinolin-4-butanamine. 3.46 g of the product of Stage C were dissolved in 70 ml of hot ethanol and 1.86 ml of hydrazine hydrate were added. The reaction medium was refluxed for 17 hours and the precipitate was eliminated by filtration. The solvent was evaporated and the residue was taken up in 70 ml of dichloromethane. Filtration was carried out and the solvent was evaporated to obtain 2.19 g of the expected product.
NMR (CDCl$_3$) ppm
1.6 (m)–1.79 (m): central CH$_2$'s; 2.75 (t): >—CH$_2$—(CH$_2$)$_3$; 3.05 (t): CH$_2$—NH$_2$; 3.95 (s): O—CH$_3$; 7.10 (d, J=4.5)–7.21 (dd)–7.92 (d)–8.71 (d, J=4.5): quinoline.

EXAMPLE 33

11,12-dideoxy-3-de-[(2,6-dideoxy-3-C-methyl-3-O-methyl-α-L-ribohexopyranosyl)-oxy)-6-O-methyl-3-oxo-12,11-oxycarbonyl-((4-(2-(2-pyridinyl)-4-thiazolyl)-butyl)-imino)]-erythromycin 705 mg of the starting compound of Example 29 (obtained as in Example 1C of the European Patent Application EP 0,596,802) in 3 ml of acetonitrile and 0.705 g of 4-(2-(2-pyridinyl-4-thiazolyl)-butanamine were heated at 60° C. for 5 hours and the reaction mixture was allowed to return to ambient temperature and was poured into water. Extraction was carried out with ethyl acetate and the extracts were washed with water and dried. The solvent was evaporated to obtain 1.8 g of product acetylated in position 2'. 15 ml of methanol were added to it and the mixture was refluxed for 2 hours and the solvent was then evaporated. The residue was chromatographed on silica (eluant: $CH_2Cl_2$—MeOH—$NH_4OH$ 95-5-0.3 then AcOEt-TEA 9-1) and crystallization from ether was carried out to obtain 194 mg of the expected product melting at 157°–159° C.
NMR ($CDCl_3$) ppm
1.33 and 1.47: 6 and 12 Me; 2.26 (s): $N(CH_3)_2$; 2.86 (t): $CH_2$—C; 3.12 (wq): $H_{10}$; 3.60 (s): $H_{11}$; 3.66 (m):

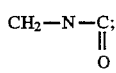

7.03 (s): thiazole $H_5$; 7.27 (ddd): pyridine $H_5$; 7.77 (dt): pyridine $H_4$; 8.18 (dd) pyridine $H_3$; 8.53 (ddd): pyridine $H_6$.

Preparation of 2-(2-pyridinyl)-thiazol-4-butanamine

Stage A: 2-aminocarbonyl-pyridine 50 ml of a diazomethane solution (0.4M/l) were added dropwise to a solution of 2 g of picolinic acid, 20 ml of dichloromethane and 5 ml of methanol and after stirring for 30 minutes at ambient temperature, the solvent was evaporated under reduced pressure. The residue was chromatographed on silica (petroleum ether (60-80)-AcOEt 5-5) to obtain 1.48 g of methyl ester. 1.42 g of the ester were heated at 50° C. for 4 hours in 5 ml of ammonium hydroxide and the reaction mixture was allowed to return to ambient temperature. Extraction was carried out with ether and the extracts were washed with water and dried. The solvent was evaporated to obtain 1.05 g of the expected product melting at 105° C.

Stage B: 2-pyridine-carbothioamide 43 g of phosphorus pentasulfide were added slowly to 46.8 g of the amide of Stage A in 700 ml of tetrahydrofuran and the mixture was stirred for 4 hours at ambient temperature. The reaction mixture was poured into water and extracted with ether. The extracts were dried and the solvent was evaporated under reduced pressure. After chromatography on silica (eluant: $CH_2Cl_2$—AcOEt 8-2), 10 g of expected product melting at 137° C. were obtained.

Stage C: ethyl 2-(2-pyridinyl)-4-thiazole-carboxylate 16.3 ml of ethyl bromopyruvate were added dropwise to 15.9 g of the product of Stage B in 250 ml of ethanol and the mixture was refluxed for 5 hours. The solvent was evaporated under reduced pressure and the residue was chromatographed on silica (eluant: hexane—AcOEt 1-1) to obtain 10.2 g of expected product melting at 69.1° C.

Stage D: 2-(2-pyridinyl)-4-thiazole-methanol 40 ml of methanol were added slowly to a mixture of 9.3 g of the ester of Stage C and 4.1 g of sodium borohydride in 100 ml of tetrahydrofuran and the mixture was refluxed for 2 hours. The reaction medium was allowed to return to ambient temperature and was poured into water and neutralized using N hydrochloric acid. Extraction was carried out with dichloromethane and the organic phase was dried. The solvent was evaporated under reduced pressure and the residue was chromatographed on silica (eluant: AcOEt—$CH_2Cl_2$ 1-1) to obtain 5.8 g of the expected product melting at 100° C.

Stage E: 2-(2-pyridinyl)-4-thiazole-carboxaldehyde 5.8 g of the product of Stage D in 60 ml of toluene were refluxed for 2 hours in the presence of 13 g of manganese oxide and filtration was carried out. The solvent was evaporated under reduced pressure to obtain 5 g of the expected product melting at 131° C.

Stage F: (Z) 2-(4-(2-(2-eyridinyl)-4-thiazolyl)-3-butenyl)-1H-isoindole-1,3(2H)-dione Using the procedure of Stage A of Preparation 32, 5.70 g of the aldehyde of Stage E and 15.9 g of the triphenylphosphonium salt of 3-bromopropyl-phosphonium and 3.70 g of potassium terbutylate were reacted to obtain 8.73 g of the expected product melting at 139°–141° C.

Stage G: (2-(4-(2-(2-pyridinyl)-4-thiazolyl)-butyl)-1H-isoindol-1,3(2H)-dione

Using the procedure of Stage B of Preparation 32, 7.22 g of the product of Stage F and 1.5 g of palladium on activated charcoal were hydrogenated for 2 hours under 1800 mbars to obtain 6.33 g of the expected product melting at 119°–121° C.

Stage H: 2-(2-pyridinyl)-thiazol-4-butanamine

Using the procedure of Stage C of Preparation 32, 5.45 g of the product of Stage G and 1.6 ml of hydrazine hydrate were refluxed for 6 hours. The solvent was evaporated and the residue was taken up in ethyl acetate and washed with water and dried. The solvent was evaporated and the residue was chromatographed on silica (eluant: $CH_2Cl_2$—MeOH—$NH_4OH$ 9-1-0.03) to obtain 1.65 g of the expected product.
NMR ($CDCl_3$) ppm
1.50 (m)–1.82 (m): central $CH_2$'s; 2.76 (t)–2.85 (t): $CH_2$—C= and $CH_2$—$NH_2$; 7.85 (s): thiazole $H_5$; 7.31 (m): H'$_5$; 7.78 (dt): H'$_4$; 8.18 (dt): H'$_3$; 8.61 (ddd): H'$_6$; 1.40 (s): $NH_2$.

EXAMPLE 34

11,12-dideoxy-3-de-[(2,6-dideoxy-3-C-methyl 3-0-methyl-α-L-ribohexopyranosyl)-oxy)-6-O-methyl-3-oxo-12,11-(oxycarbonyl-((4-(4-(3-pyridinyl)-1H-imidazol-1-yl)-butyl)-imino)]-erythromycin 1 g of the starting compound of Example 29 (obtained as in Example 1C of the European Patent application EP 0,596,802) in 4 ml of acetonitrile and 936 mg of 4-(4-(3-pyridinyl-1H-imidazol-1-yl)-butanamine were heated at 70° C. for 20 hours and the reaction medium was allowed to return to ambient temperature and was poured into water. Extraction was carried out with ethyl acetate and the extracts were washed with water and dried. The solvent was evaporated to obtain 1.34 g of product acetylated in position 2'. 40 ml of methanol were added to it and the mixture was stirred for 2 hours. The solvent was evaporated and the residue was chromatographed on silica (eluant: $CH_2Cl_2$—MeOH—$NH_4OH$ 95-5-0.4). Crystallization from ether yielded 310 mg of the expected product melting at 187°–188° C.
NMR ($CDCl_3$) ppm
0.83 (t): $CH_3$—$CH_2$; 1.01 (d)–1.17 (d)–1.25 (d)–1.31 (d)–1.38 (d): the $CH_3$—CH's; 1.34 (s)–1.47 (s): 6 and 12 Me; 2.27 (s): N(Me)$_2$; 2.45 (m): H'$_3$; 2.62 (s): 6-OMe; 2.60 (m): $H_8$; 2.85 to 3.25: $H_4$ and $H_{10}$, H'$_2$; 3.52 (m): $H_5$; 3.56 (s): $H_{11}$; 3.60 to 3.85 (m):

4.23 (d): $H_5$; 4.27 (d): H'$_1$; 4.93 (dd): $H_{13}$; 7.29 (ddd): pyridine $H_5$; 8.08 (dt): pyridine $H_4$; 8.45 (dd): pyridine $H_6$; 8.97 (dd): pyridine $H_2$; 7.35 (d) and 7.53 (d): imidazole $H_2$ and $H_5$.

Preparation of 4-(3-pyridinyl)-1H-imidazol-1-butanamine

Stage A: 2-(4-(3-pyridinyl)-1H-imidazol-1-yl)-butyl-1H-iso-indol-1,3(2H)-dione

Using the procedure of Stage A of Example 1, 290 mg of 3-pyridinyl-1H-imidazole [prepared as in J. Chem. Soc., pp. 753–5 (1938)], 115 mg of sodium hydride and 633 mg of N-bromaobutyl phthalimaide were reacted to obtain 277 mg of the expected product melting at 150°–152° C.

Stage B: 4-(3-pyridinyl)-1H-imidazol-1-butanamaine

Using the procedure of Stage B of Example 1, 1.66 g of the product of Stage A and 0.46 ml of hydrazine hydrate in 30 ml of ethanol were reacted to obtain 936 mag of the desired product which was used as is for the synthesis.

NMR ($CDCl_3$) ppm 1.49 (m)–1.89 (m): the central $CH_2$'s; 2.75 (t): $CH_2$—$CH_2$—N; 4.01 (t):

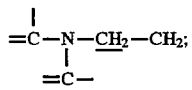

7.29 (d, J=1)–7.55 (d, J=1): $H_2$ and $H_5$; 7.30 (partly masked): $H'_5$; 8.09 (dt, J=8 and 2): $H'_4$; 8.47 (dd, J=5 and 2): $H'_6$; 8.96 (d, J=2): $H'_2$; 1.49 (ws): approx. mobile 2H's.

EXAMPLE 35

11,12-dideoxy-3-de-[(2,6-dideoxy-3-C-methyl-3-O-methyl-α-L-ribohexopyranosyl)-oxy)-6-O-methyl-3-oxo-12,11-oxycarbonyl-((4-(3-(3-pyridinyl)-1H-1,2,4-triazol-1yl)-butyl)-imino)]-erythromycin 1g of the starting compound of Example 29 (obtained as in Example 1C of the European Patent Application EP 0,596,802) in 4 ml of acetonitrile and 1.21 g of 4-(3-(3-pyridinyl 1H-1,2,4-triazol-1-yl)-butanamine were heated at 75° C. for 8 hours and then the reaction medium was allowed to return to ambient temperature and was poured into water. Extraction was carried out with ethyl acetate and the extracts were washed with water and dried. The solvent was evaporated to obtain 2 g of product acetylated in position 2 '. 40 ml of methanol were added to it and the mixture was stirred for 16 hours. The solvent was evaporated and the residue was chromatographed on silica (eluant: $CH_2Cl_2$—MeOH—$NH_4OH$ 90-10-0.04). Crystallization from ether yielded 292 mg of the expected product melting at 190°–192° C.

NMR ($CDCl_3$) ppm 0.84 (t): $CH_3$—$CH_2$; 1.01 (d): OMe; 1.16 (d): 8Me; 1.25 (d): 5Me; 1.30 (d): 4Me; 1.34 (d): 2Me; 1.33 (s) and 1.47 (s): 6 and 12 Me; 1.67 (m)–1.99 (m): the central $CH_2$'s; 2.26 (s): $N(Me)_2$; 2.44 (m): $H'_3$; 2.58 (m): $H_8$; 2.61 (s): 6—OMe; 3.06 (m): $H_4$; 3.12 (q): $H_{10}$; 3.17(dd): $H'_2$; 3.52 (m): $H'_5$; 3.56 (s): $H_{11}$; 3.64 to 3.75 (–):

3.85 (q): $H_2$; approx. 4.25: $H'_1$, $H_5$ and

4.91 (dd): $H_{13}$; 8.15 (s): triazole H; 7.35 (dd): pyridine $H_5$; 8.34 (dt): pyridine $H_4$; 8.62 (dd): pyridine $H_6$; 9.31 (wd): pyridine $H_2$.

Preparation of 3-(3-pyridinyl)-1H-1,2,4-triazol-1-butanamine

Stage A: 2-(4-(3-(3-pyridinyl)-1H-1,2,4-triazol-1-yl)-butyl-1H-isoindol-1,3(2H)-dione Using the procedure of Stage A of Example 1, 2.1 g of 3-pyridinyl-1H-1,2,4-triazole prepared as in J. Org. Chem., Vol. (44) No. 33, pp. 4160–4164 (1979), 1.02 g of sodium hydride and 4.13 g of N-4-bromobutyl phthalimide were reacted to obtain 2.4 g of the expected product melting at 150°–152°C.

Stage B: 3-(3-pyridinyl)-1H-1,2,4-triazol-1-butanamine (fumarate)

Using the procedure of Stage B of Example 1, 3.46 g of the product of Stage A and 1 ml of hydrazine hydrate in 50 ml of ethanol were reacted to obtain 2.1 g of crude product which was converted into the fumarate as in Preparation 30 to obtain 1.13 g of the fumarate of the expected product is obtained melting at approx. 190°–192° C.

NMR ($CDCl_3$) ppm 1.50 (m)–2.01 (m): the central $CH_2$'s; 2.76 (t): $NH_2$—$CH_2$—; 4.24: =N—N—$CH_2$; 7.37 (ddd): $H_5$; 8.35 (dt): $H_4$; 8.63 (dd): $H_6$; 9.32 (dd): $H_2$; 8.12 (s): triazole =CH.

Operating as previously using the appropriate amines, the following products were prepared:

EXAMPLE 36

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(3-quinolinyl)-butyl)-imino)]-erythromycin melting at 190°–192° C.

EXAMPLE 37

11,12-dideoxy-3-de((2,6-dideoxy-3-C-methyl-3-O-methyl-α-L-ribohexopyranosyl)-oxy)-6-O-methyl-3-oxo-12,11-(oxycarbonyl-((4-(4-(4-methoxyphenyl)-1H-imidazol-1-yl)-butyl)-imino)]-erythromycin melting at 152°–154° C.

EXAMPLE 38

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(2-phenyl-4-thiazolyl)-butyl)-imino)]-erythromycin melting at 141°–143° C.

EXAMPLE 39

11,12-dideoxy 3-de-[(2,6-dideoxy-3-C-methyl-3-O-methyl-α-L-ribohexopyranosyl)-oxy)-6-O-methyl-3-oxo-12,11-(oxycarbonyl-((4-(4-(3-methoxyphenyl)-1H-imidazol-1-yl)-butyl)-imino)]-erythromycin melting at 144°–146° C.

EXAMPLE 40

11,12-dideoxy-3-de[(2,6-dideoxy-3-C-methyl-3-O-methyl-α-L-ribohexopyranosyl)-oxy)-6-O-methyl-3-oxo-2,11-(oxycarbonyl-((4-(4,5-diphenyl)-1H-imidazol-1-yl)-butyl)-imino)]-erythromycin melting at 180°–182° C.

EXAMPLE 41

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-quinazolinyl)-butyl)-imino)]-erythromycin melting at 212°–214° C.

EXAMPLE 42

11,12-dideoxy-3-de-[(2,6-dideoxy-3-C-methyl-3-O-methyl-α-L-ribohexopyranosyl)-oxy)-6-O-methyl-3-oxo- 12,11-(oxycarbonyl-((4-(2-(4-pyridinyl)-4-thiazolyl)-butyl)-imino)]-erythromycin melting at 192°–194° C.

EXAMPLE 43

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(1,2,3,6-tetrahydro-1,3-dimethyl-2,6-dioxo-7H-purin-7-yl)-butyl)-imino)]-erythromycin melting at 251°–253° C.

EXAMPLE 44

11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(4-trifluoromethoxy)-phenyl)-1H-imidazol-4-yl)butyl)-imino)]-erythromycin melting at 168°–170° C.

The amines used as starting products were prepared by the following methods:

A—When the chain is attached to a carbon such as

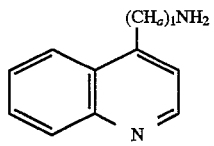

one can start with the corresponding aldehydes in the following equation

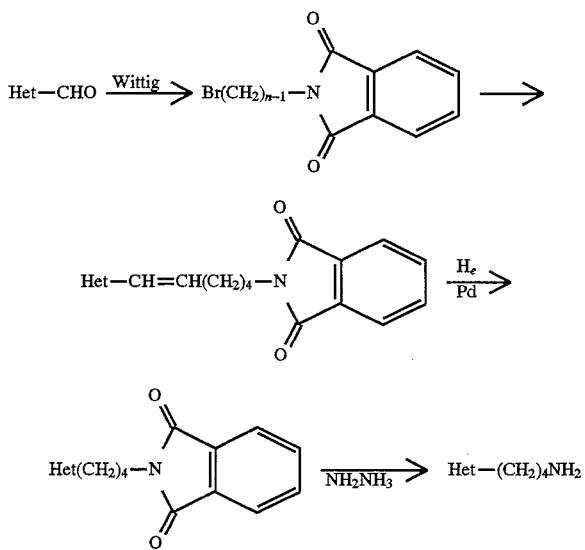

The amines used for the preparation of the products of Examples 4, 8, 11, 12, 18, 19, 23 and 24 were prepared in this way.

B—When the chain is attached to a nitrogen, the amines can be prepared in the following way:

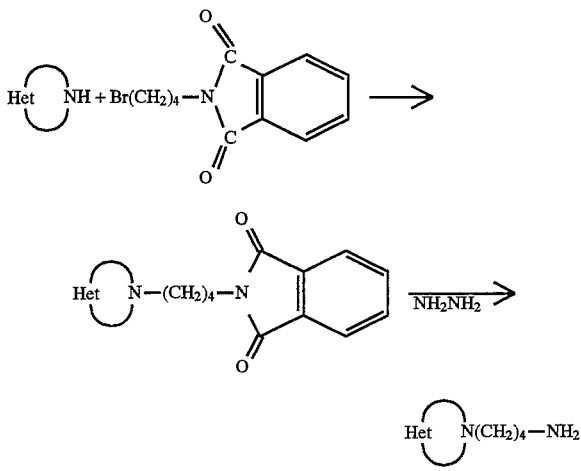

The amines used for the preparation of the products of Examples 1, 2, 3, 5, 9, 13, 14, 15, 16, 17, 20, 21, 22, 25, 26 and 28 were prepared in this way.

C—Certain amines were prepared in a particular way with the heterocycle constructed and the chain introduced at the same time (Example 6, 7, 10 and 27).

Examples of Pharmaceutical Compositions

Compositions were prepared containing 150 mg of the Product of Example 1 or 2 or 3 and sufficient excipient of starch, talc and magnesium stearate for 1 g.

Pharmacological Study of the Products of the Invention

Method of Dilutions in Liquid Medium

A series of tubes were prepared into which an equal quantity of sterile nutritive medium was divided. Increasing quantities of the product to be studied were distributed into each tube and then each tube was seeded with a bacterial strain. After incubation for twenty-four hours in an oven at 37° C., the growth inhibition was evaluated by trans-illumination which permitted the minimal inhibiting concentrations (M.I.C.) to be determined expressed in micrograms/ml. The following results were obtained:

| Products | GRAM+ bacterial strains | | | | | | | |
|---|---|---|---|---|---|---|---|---|
| | Ex. 1 | Ex. 2 | Ex. 3 | Ex. 29 | Ex. 31 | Ex. 32 | Ex. 34 | Ex. 35 |
| Staphylococcus aureus 011UC4 | 0,04 | 0,04 | 0,08 | 0,04 | 0,04 | 0,08 | 0,04 | 0,08 |
| Staphylococcus aureus 011G025I | 0,08 | 0,15 | 0,15 | 0,15 | 0,08 | 0,15 | 0,08 | 0,6 |
| Staphylococcus epidermidis 012G011I | 0,08 | 0,04 | 0,15 | 0,04 | 0,4 | 0,08 | 0,04 | — |

-continued

| Products | GRAM+ bacterial strains | | | | | | | |
|---|---|---|---|---|---|---|---|---|
| | Ex. 1 | Ex. 2 | Ex. 3 | Ex. 29 | Ex. 31 | Ex. 32 | Ex. 34 | Ex. 35 |
| *Streptococcus pyogenes* group A 02A1UC1 | 0,04 | ≦0,02 | 0,04 | ≦0.02 | ≦0.02 | ≦0,02 | ≦0,02 | ≦0.02 |
| *Streptococcus agalactiae* group B 02B1HT1 | ≦0,02 | ≦0,02 | ≦0,02 | ≦0,02 | ≦0,02 | ≦0,02 | ≦0,02 | ≦0,02 |
| *Streptococcus faecalis* group D 02D2UC1 | 0,04 | ≦0,02 | 0,04 | ≦0,02 | ≦0,02 | ≦0,02 | ≦0,02 | ≦0,02 |
| *Streptococcus faecium* group D 02D3HT1 | ≦0,02 | ≦0,02 | 0,04 | ≦0,02 | ≦0,02 | ≦0,02 | 0,3 | ≦0,02 |
| Streptococcus sp group G 02G0GR5 | 0,04 | ≦0,02 | 0,04 | ≦0,02 | ≦0,02 | ≦0,02 | ≦0,02 | ≦0,02 |
| *Streptococcus mitis* 02mitCB1 | ≦0,02 | ≦0,02 | 0,02 | ≦0,02 | ≦0,02 | ≦0,02 | ≦0,02 | ≦0,02 |
| *Streptococcus mitis* 02mitGR16I | ≦0,02 | 0,15 | 0,04 | ≦0,02 | ≦0,02 | ≦0,02 | ≦0,02 | 0,02 |
| *Streptococcus agalactiae* group B 02B1SJ1 | 0,08 | 0,08 | 0,04 | — | 0,08 | 0,04 | 0,04 | 0,08 |
| *Streptococcus pneumonias* 030SJ5 | 0,04 | 0,04 | 0,15 | 0,04 | 0,15 | 0,15 | ≦0,02 | ≦0,02 |

Various modifications of the compounds and method of the invention may be made without departing from the spirit or scope thereof and it is to be understood that the invention is intended to be limited only as defined in the appended claims.

What we claim is:

1. A compound of the formula

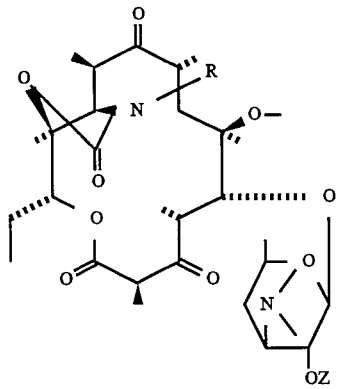

I wherein R is

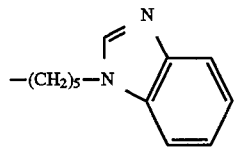

or —(CH₂)ₙ—Ar, n is an integer from 3 to 5, Ar is an optionally substituted heterocyclic selected from the group consisting of

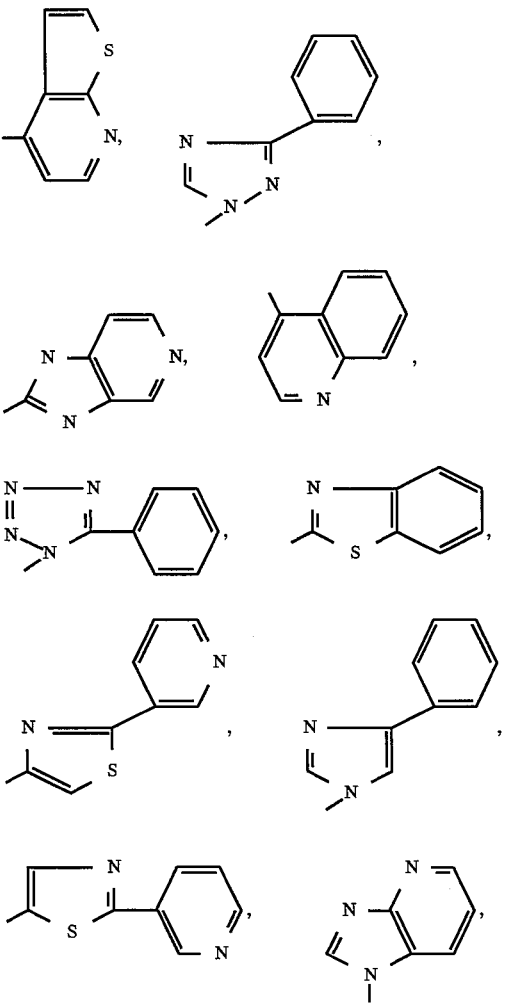

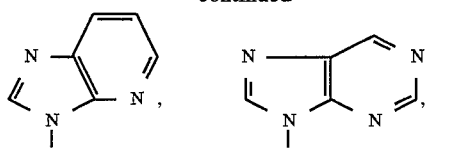
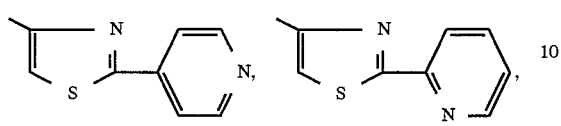
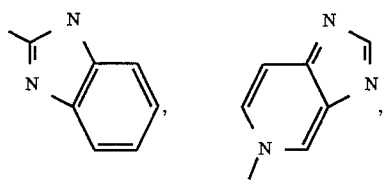
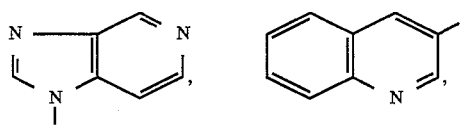
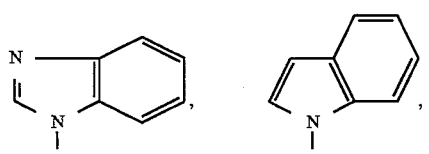
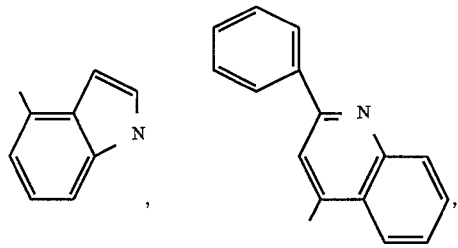
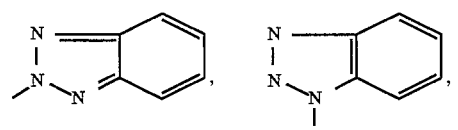
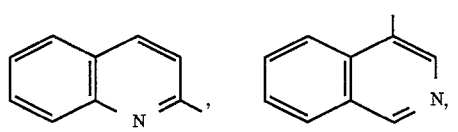
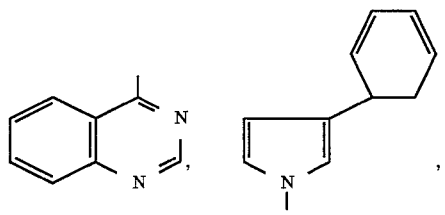

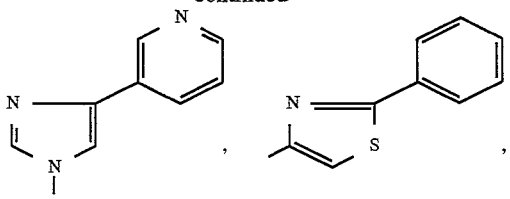
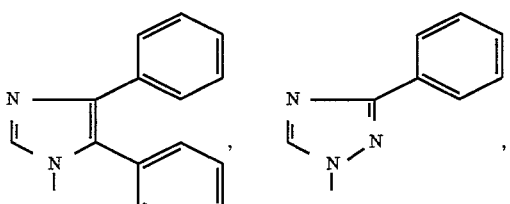
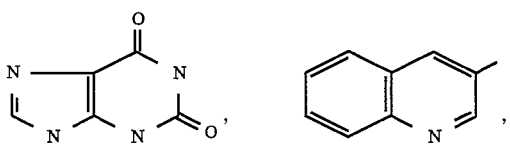
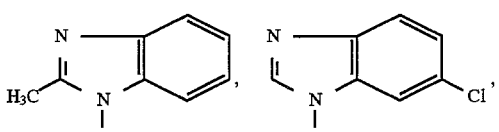

and 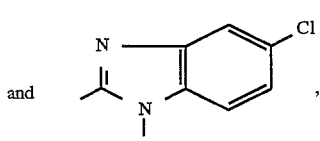, the optional substituents are at least one member selected from the group consisting of a free, salified, esterified and amidified carboxyl, hydroxyl, halogen, —NO₂, —CN, alkyl, cycloalkyl, alkenyl, alkynyl, O-alkyl, O-alkenyl, O-alkynyl, S-alkyl, S-alkenyl, S-alkynyl, N-alkyl, N-alkenyl and N-alkynyl of up to 12 carbon atoms optionally substituted by one or more halogens, b) 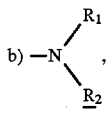

$R_1$ and $R_2$ are individually hydrogen or alkyl of up to 12 carbon atoms, c) 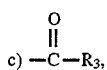

$R_3$ is alkyl of up to 12 carbon atoms, and d) an optionally substituted carbocyclic O-aryl and S-aryl and heterocyclic aryl, O-aryl and S-aryl and Z is hydrogen or an acid remainder or its non-toxic, pharmaceutically acceptable acid addition salts.

2. A compound of claim 1 wherein Z is hydrogen.

3. A compound of claim 1 wherein Z is 4.

4. A compound of claim 1 wherein Ar is

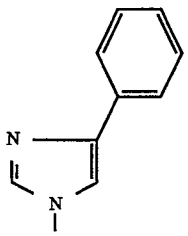

optionally substituted.

5. A compound of claim 1 wherein Ar is

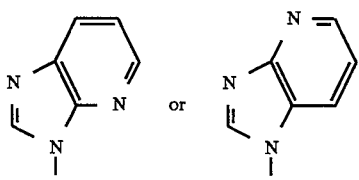

optionally substituted.

6. A compound of claim 1 wherein Ar is selected from the group consisting of

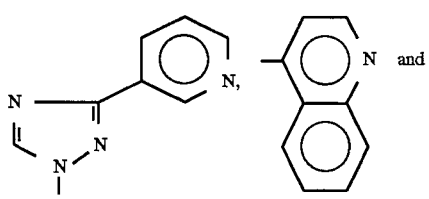

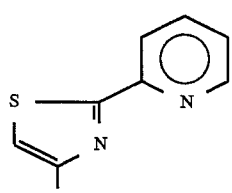

optionally substituted.

7. A compound of claim 1 wherein Ar is

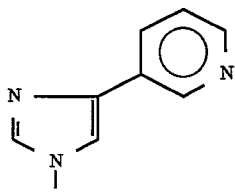

optionally substituted.

8. A compound of claim 1 selected from the group consisting of 11,12-dideoxy-3-de-[(2,6-dideoxy-3-C-methyl-3-O-methyl-α-L-ribohexopyranosyl)-oxy)- 6-O-methyl-3-oxo-12,11-(oxycarbonyl-((4-(4-phenyl-1H-imidazol-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(3H-imidazo(4,5-b)pyridin-3-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(1H-imidazo(4,5-b)pyridin-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(4-chlorophenyl)-1H-imidazol-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(2-methoxyphenyl)-1H-imidazol-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(4-fluorophenyl)-1H-imidazol-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(7-methoxy-4-quinoleinyl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(2-(2-pyridinyl)-4-thiazolyl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(3-(3-pyridinyl)-1H-1,2,4-triazol-1-yl)-butyl)-imino)]-erythromycin, and their non-toxic, pharmaceutically acceptable acid addition salts.

9. A compound of claim 1 which is 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(3-pyridinyl)-1H-imidazol-1-yl)-butyl)-imino)]-erythromycin.

10. An antibacterial composition comprising an antibiotically effective amount of a compound of claim 1 and an inert pharmaceutical carrier.

11. A method of treating bacterial infections in warm-blooded animals comprising administering to warm-blooded animals having a bacterial infection an antibiotically effective amount of a compound of claim 1.

12. A method of claim 11 wherein Z is hydrogen.

13. A method of claim 11 wherein n is 4.
14. A method of claim 11 wherein Ar is

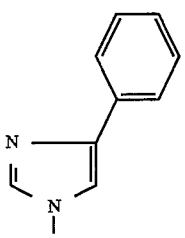

optionally substituted.

15. A method of claim 11 wherein Ar is

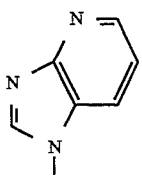

or

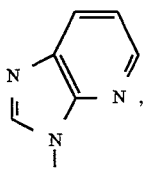

optionally substituted.

16. A method of claim 11 wherein Ar is selected from the group consisting of

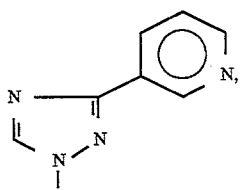

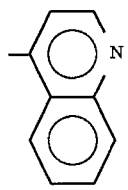

and

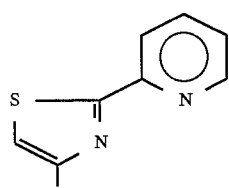

optionally substituted.

17. A method of claim 11 wherein Ar is

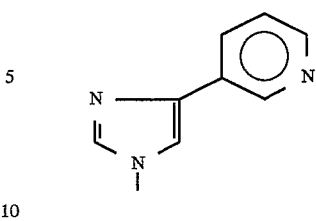

optionally substituted.

18. A method of claim 11 wherein the compound is selected from the group consisting of 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-phenyl-1H-imidazol-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(3H-imidazo(4,5-b)pyridin-3-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(1H-imidazo(4,5-b)pyridin-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(4-chlorophenyl)-1H-imidazol-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(2-methoxyphenyl)-1H-imidazol-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(4-fluorophenyl)-1H-imidazol-1-yl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(7-methoxy-4-quinoleinyl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(2-(2-pyridinyl)-4-thiazolyl)-butyl)-imino)]-erythromycin, 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(3-(3-pyridinyl)-1H-1,2,4-triazol-1-yl)-butyl)-imino)]-erythromycin, and their non-toxic, pharmaceutically acceptable acid addition salts.

19. A method of claim 11 wherein the compound is 11,12-dideoxy-3-de-[(2,6-dideoxy-3-C-methyl-3-O-methyl-α-L-ribohexopyranosyl)-oxy)-6-O-methyl-3-oxo-12,11-(oxycarbonyl-((4-(4-(3-pyridinyl)-1H-imidazol-1-yl)-butyl)-imino)]-erythromycin.

* * * * *

UNITED STATES PATENT AND TRADEMARK OFFICE
CERTIFICATE OF CORRECTION

PATENT NO. : 5,635,485
DATED : June 3, 1997
INVENTOR(S) : Constantin Agouridas et al.

It is certified that error appears in the above-identified patent and that said Letters Patent is hereby corrected as shown below:

Column 28,
Line 67, delete "Z" and insert -- n --.

Signed and Sealed this

Twentieth Day of July, 2004

JON W. DUDAS
*Acting Director of the United States Patent and Trademark Office*